United States Patent
Shima et al.

(10) Patent No.: US 9,868,701 B2
(45) Date of Patent: Jan. 16, 2018

(54) METHOD FOR PRODUCING NITROGEN-CONTAINING PENTAFLUOROSULFANYLBENZENE COMPOUND

(71) Applicant: UBE INDUSTRIES, LTD., Yamaguchi (JP)

(72) Inventors: Hidetaka Shima, Yamaguchi (JP); Youji Omata, Yamaguchi (JP)

(73) Assignee: UBE INDUSTRIES, LTD. (JP)

( * ) Notice: Subject to any disclaimer, the term of this patent is extended or adjusted under 35 U.S.C. 154(b) by 0 days.

(21) Appl. No.: 15/539,059

(22) PCT Filed: Dec. 25, 2015

(86) PCT No.: PCT/JP2015/086177
§ 371 (c)(1),
(2) Date: Jun. 22, 2017

(87) PCT Pub. No.: WO2016/104677
PCT Pub. Date: Jun. 30, 2016

(65) Prior Publication Data
US 2017/0349545 A1    Dec. 7, 2017

(30) Foreign Application Priority Data
Dec. 25, 2014   (JP) .................................. 2014-263240

(51) Int. Cl.
*C07C 381/00* (2006.01)
*C07D 207/40* (2006.01)

(52) U.S. Cl.
CPC .......... *C07D 207/40* (2013.01); *C07C 381/00* (2013.01)

(58) Field of Classification Search
CPC ............................ C07D 207/40; C07C 381/00
See application file for complete search history.

(56) References Cited

U.S. PATENT DOCUMENTS 4,873,338 A   10/1989  Euskirchen et al.
6,410,737 B1  6/2002   Ancel et al.
(Continued)

FOREIGN PATENT DOCUMENTS

JP   59-231028 A   12/1984
JP   63-156759 A   6/1988
(Continued)

OTHER PUBLICATIONS

International Search Report for PCT/JP2015/086177 dated Mar. 15, 2016, 2 pages.

*Primary Examiner* — Shawquia Jackson
(74) *Attorney, Agent, or Firm* — Swanson & Bratschun, L.L.C.

(57) ABSTRACT

A method for producing a nitrogen-containing pentafluoro-sulfanylbenzene compound of formula (2a) or (2b):

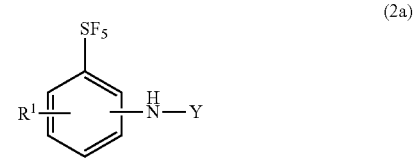

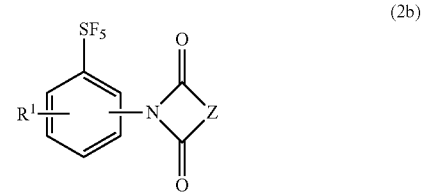

(wherein $R^1$ a hydrogen atom or a hydrocarbon group; Z is an aryl group linked to a carbonyl group; Y is a group of formula (Y1), (Y2), (Y3), or (Y4); $R_2$ is a hydrogen atom or a hydrocarbon group)

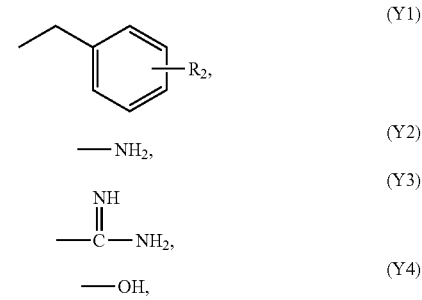

the method comprising reacting a halogeno-pentafluoro-sulfanylbenzene compound of formula (1) with a nitrogenous nucleophile:

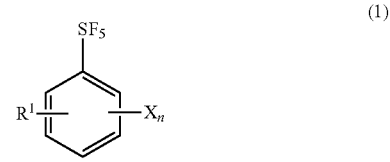

(wherein X is a halogen atom; n is an integer of 1 to 5; $R^1$ is as defined above).

8 Claims, No Drawings

(56) References Cited

U.S. PATENT DOCUMENTS

| | | |
|---|---|---|
| 2005/0148652 A1 | 7/2005 | Kleemann et al. |
| 2008/0091031 A1 | 4/2008 | Kleemann et al. |
| 2012/0129846 A1* | 5/2012 | Zhu .................... C07D 413/10 514/230.2 |
| 2012/0130128 A1 | 5/2012 | Gottel et al. |

FOREIGN PATENT DOCUMENTS

| | | |
|---|---|---|
| JP | 11-012239 A | 1/1999 |
| JP | 2002-541131 A | 12/2002 |
| JP | 2007-512246 A | 5/2007 |
| JP | 2013-544774 A | 12/2013 |
| WO | WO 2000/059862 A2 | 12/2000 |
| WO | WO 2005/047240 A1 | 5/2005 |

\* cited by examiner

METHOD FOR PRODUCING NITROGEN-CONTAINING PENTAFLUOROSULFANYLBENZENE COMPOUND

RELATED APPLICATIONS

This application is a 35 U.S.C. §371 national phase application of International Application Serial No. PCT/JP2015/086177, filed Dec. 25, 2015 (WO 2016/104677). International Application Serial No. PCT/JP2015/086177 claims the benefit of Application Serial No. JP 263240/2014, filed Dec. 25, 2014, which is incorporated herein by reference in its entirety.

TECHNICAL FIELD

The present invention relates to a method for producing a nitrogen-containing pentafluorosulfanylbenzene compound, comprising reacting a halogenated aromatic compound with a nitrogenous nucleophile.

BACKGROUND ART

Aromatic amine compounds like aniline are compounds that are useful mainly as base materials for pharmaceuticals, agricultural chemicals, and dyes.

It was known that pentafluorosulfanylaniline compounds can be produced by reacting a disulfide compound with a fluorine gas (Patent Literature 1). This method was found to have some problems, because a fluorine gas which is problematic in handling must be used, and because with the progress of the fluorination of the benzene nucleus, the resulting nucleus fluorine compound becomes difficult to remove. For these reasons, it is difficult to produce these compounds by this method, and thus this method was hardly adopted as an industrial production method.

CITATION LIST

Patent Literature

Patent Literature 1: Japanese Patent No. JP 3964935

SUMMARY OF INVENTION

Technical Problem

An object of the present invention resides in providing a method for producing a nitrogen-containing pentafluorosulfanylbenzene compound according to a simple technique using easy-to-obtain source materials.

Solution to Problem

The aforementioned object is achieved by the present invention described below.

[1] A method for producing a nitrogen-containing pentafluorosulfanylbenzene compound of formula (2a) or (2b):

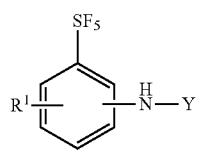
(2a)

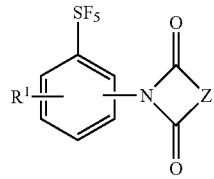
(2b)

(wherein $R^1$ a hydrogen atom or a hydrocarbon group; Z is an aryl group linked to a carbonyl group; Y is a group of formula (Y1), (Y2), (Y3), or (Y4); $R_2$ is a hydrogen atom or a hydrocarbon group)

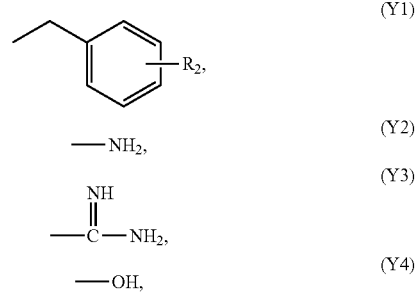

the method comprising reacting a halogeno-pentafluorosulfanylbenzene compound of formula (1) with a nitrogenous nucleophile:

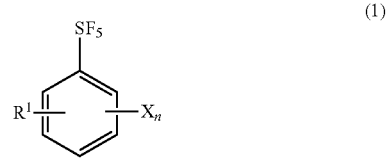
(1)

(wherein X is a halogen atom; n is an integer of 1 to 5; $R^1$ is as defined above).

[2] A method for producing a pentafluorosulfanylaniline compound of formula (3):

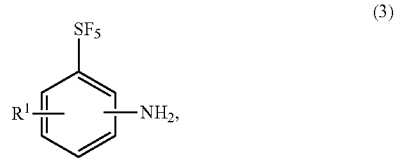
(3)

the method comprising reducing or hydrolyzing the nitrogen-containing pentafluorosulfanylbenzene compound as set forth in [1].

[3] The method as set forth in [1] or [2], wherein the nitrogenous nucleophile is at least one member selected from benzylamine compounds, hydrazine compounds, guanidine compounds, hydroxylamines and alkali metal salts of phthalimide.

[4] The method as set forth in [2] or [3], wherein the reduction is carried out in the presence of hydrogen using Pd/C or Raney nickel as a catalyst.

[5] The method as set forth in any of [2] to [4], wherein the hydrolysis is carried out using an aqueous acid solution or an aqueous alkali solution.

[6] The method as set forth in any of [1] to [5], wherein an aprotic polar solvent is used as a solvent.

[7] The method as set forth in [6], wherein the aprotic polar solvent is dimethyl sulfoxide or N-methyl-2-pyrrolidone.

[8] The method as set forth in any of [1] to [7], wherein a base is used in the reaction of the halogeno-pentafluorosulfanylbenzene compound with the nitrogenous nucleophile.

Advantageous Effects of Invention

The present invention can provide a method for producing a nitrogen-containing pentafluorosulfanylbenzene compound according to a simple technique using easy-to-obtain source materials.

DESCRIPTION OF EMBODIMENTS

Hereunder, the present invention will be described in detail. As referred to in this invention, the range "X to Y" shall include the endpoint values X and Y.

As referred to in the present invention, the "nitrogen-containing pentafluorosulfanylbenzene compound" refers to a pentafluorosulfanylbenzene compound having an amino group or an imide group. A method for producing this compound comprises the step of reacting a halogeno-pentafluorosulfanylbenzene compound with a nitrogenous nucleophile. Hereinafter, this step may also be referred to as a "nucleophilic reaction step".

The halogeno-pentafluorosulfanylbenzene compound used in the present invention is represented by formula (1) as shown below:

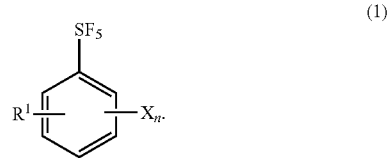

(1)

In this formula, X is a halogen atom, and n represents an integer of 1 to 5. Examples of the halogen include, but are not limited to, fluorine, chlorine, bromine, and iodine, with fluorine and chlorine being preferred, and fluorine being more preferred.

The number n of halogen substituents is an integer of 1 to 5. Compound (1) may have a plurality of different halogen atoms that differ in reactivity in nucleophilic reaction. However, from various viewpoints including ease of handling, it is preferred that n be 1 (i.e., X is monosubstituted).

Examples of the position at which the halogen is substituted include ortho, meta, and para positions. In various viewpoints including reactivity, the position at which the halogen is substituted is preferably a meta position or a para position, more preferably a para position, relative to the pentafluorosulfanyl group.

$R^1$ is a hydrocarbon group or a hydrogen atom. Examples of this substituent include alkyl or aryl groups that are nonreactive with a nitrogenous nucleophile, but it is preferred that $R^1$ be a hydrogen atom.

Examples of the nitrogenous nucleophile include, but are not limited to, benzylamine compounds (e.g., benzylamine, p-chlorobenzylamine, p-methoxybenzylamine), hydrazine compounds (e.g., hydrazine anhydride, hydrazine hydrate, hydrogen halide salt of hydrazine), guanidine compounds (e.g., guanidine carbonate, hydrogen halide salt of guanidine), hydroxylamine compounds (e.g., hydroxylamine anhydride, hydroxylamine hydrate, hydrogen halide salt of hydroxylamine), and alkali metal salts of phthalimide (e.g., potassium phthalimide).

The amount of the nitrogenous nucleophile used is in the range of 0.1 to 100 mol, preferably in the range of 1.0 to 50 mol, particularly preferably in the range of 1.1 to 10 mol, relative to 1 mol of the halogeno-pentafluorosulfanylbenzene compound.

This nucleophilic reaction may be carried out in the absence of a solvent, but is preferably carried out using a solvent.

The solvent is preferably an aprotic polar solvent, and is particularly preferably dimethyl sulfoxide or N-methyl-2-pyrrolidone.

In this nucleophilic reaction, an organic or inorganic base may be used.

Examples of the organic base include tertiary amines such as triethylamine and tributylamine Examples of the inorganic base include carbonates such as lithium carbonate, potassium carbonate, and cesium carbonate. However, the inorganic base is preferred, and potassium carbonate is particularly preferred.

The amount of the base used is in the range of 0.1 to 100 mol, preferably in the range of 1.0 to 50 mol, particularly preferably in the range of 1.1 to 10 mol, relative to 1 mol of the halogeno-pentafluorosulfanylbenzene compound.

The reaction temperature of this nucleophilic reaction is in the range of 0 to 200° C., preferably in the range of 20 to 150° C.

When the reaction is carried out using 4-fluoro-pentafluorosulfanylbenzene as a halogeno-pentafluorosulfanylbenzene compound, and benzylamine as a nitrogenous nucleophile, N-benzyl-4-pentafluorosulfanylbenzene (a compound of formula (1a) wherein Y is formula (Y1)) is produced. In formula Y1, $R_2$ is a hydrogen atom or a hydrocarbon group such as aryl group or alkyl group. From various viewpoints including enhancement of this nucleophilic reaction and atom efficiency, it is preferred that $R_2$ be a hydrogen atom or an alkyl group having 1 to 5 carbon atoms.

When the reaction is likewise carried out using a hydrazine compound as a nitrogenous nucleophile, (4-pentafluorosulfanylphenyl)hydrazine (a compound of formula (1a) wherein Y is formula (Y2)) is produced. When the reaction is likewise carried out using a guanidine compound as a nitrogenous nucleophile, (4-pentafluorosulfanylphenyl)guanidine (a compound of formula (1a) wherein Y is formula (Y3)) is produced. When the reaction is likewise carried out using a hydroxylamine compound as a nitrogenous nucleophile, N-(4-pentafluorosulfanylphenyl)hydroxylamine (a compound of formula (1a) wherein Y is formula (Y4)) is produced.

When the reaction is likewise carried out using potassium phthalimide as a nitrogenous nucleophile, N-(4-pentafluorosulfanylphenyl)phthalimide (a compound of formula (1b) wherein Z is an aryl group (phenylene group)) is produced. Examples of the aryl group include substituted or unsubstituted phenylene or naphthylene groups, but from various viewpoints including ease of obtaining the compound, an unsubstituted phenylene group is preferred.

When the reaction is carried out using 2-fluoro-pentafluorosulfanylbenzene as a halogeno-pentafluorosulfanylbenzene compound, and benzylamine as a nitrogenous nucleophile, N-benzyl-2-pentafluorosulfanylbenzene is produced. When the reaction is likewise carried out using a hydrazine compound as a nitrogenous nucleophile, (2-pentafluorosulfanylphenyl)hydrazine is produced. When the reaction is likewise carried out using a guanidine compound as a nitrogenous nucleophile, (2-pentafluorosulfanylphenyl)guanidine is produced. When the reaction is likewise carried out using a hydroxylamine compound as a nitrogenous nucleophile, N-(2-pentafluorosulfanylphenyl)hydroxylamine is produced. When the reaction is likewise carried out using potassium phthalimide as a nitrogenous nucleophile, N-(2-pentafluorosulfanylphenyl)phthalimide is produced.

Likewise, when the reaction is carried out using 3-fluoropentafluorosulfanylbenzene as a halogeno-pentafluorosulfanylbenzene compound, (3-pentafluorosulfanylphenyl)hydrazine and other like compounds can be produced. Typical specific examples of those compounds are shown below.

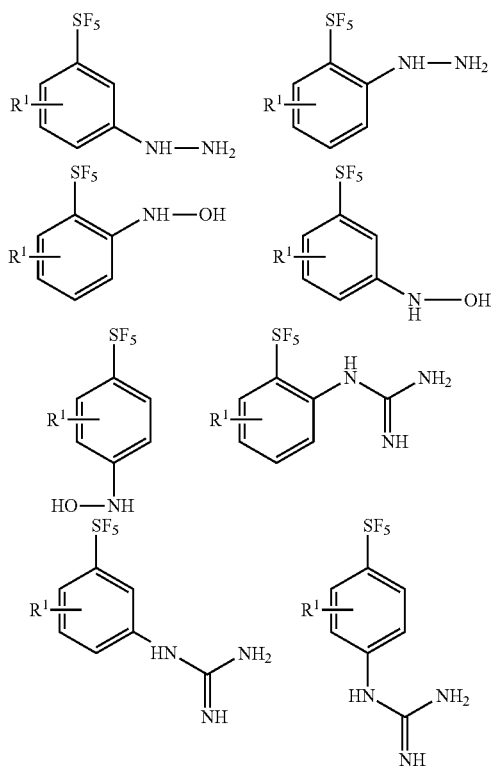

The resulting product can be used, after or without being purified, as a source material for use at the subsequent reduction step. The step of reducing the product may also be referred to as a "reduction step".

By reducing the product N-benzyl-4-pentafluorosulfanylbenzene obtained by the previous nucleophilic reaction, 4-pentafluorosulfanylaniline (a compound of formula (3)) is produced. It is preferred that before the reduction step, a reaction mixture containing N-benzyl-4-pentafluorosulfanylbenzene should be, for example, crystallized in a water/methanol solvent, dissolved in solvent, filtered over activated carbon, and crystallized again in a water/methanol solvent. It is preferable to purify the reaction product by column chromatography. Alternatively, it is preferable to add a nitrogenous nucleophile like hydrazine. In the previous nucleophilic reaction mentioned above, there may be produced traces of byproducts that significantly interfere with the reduction with a Pd/C catalyst used at the subsequent step. Such byproducts can be degraded or removed in the reaction system by adding a nitrogenous nucleophile.

The reduction can be carried out by dissolving the product obtained at the previous step in a solvent, adding a catalyst, and reacting the mixture in the presence of hydrogen.

By reducing the product (4-pentafluorosulfanylphenyl)hydrazine obtained by the previous nucleophilic reaction, 4-pentafluorosulfanylaniline is produced. It is preferred that before the reduction step, a reaction mixture containing (4-pentafluorosulfanylphenyl)hydrazine should be, for example, crystallized in a water solvent or dissolved in an organic solvent, and washed with acid, alkali, and water. The reaction product can also be purified by column chromatography. The reduction can be carried out by dissolving the product obtained at the previous step in a solvent, adding a catalyst, and reacting the mixture in the presence of hydrogen.

Examples of the solvent used at the nucleophilic reaction and reduction steps include: alcohols such as methanol, ethanol, isopropyl alcohol, butyl alcohol, ethylene glycol, diethylene glycol, and triethylene glycol; ketones such as acetone, methyl ethyl ketone, and methyl isobutyl ketone; amides such as N,N-dimethylformamide, N,N-dimethylacetamide, and N-methylpyrrolidone; ureas such as N,N'-dimethylimidazolidinone; sulfoxides such as dimethyl sulfoxide; nitriles such as acetonitrile, propionitrile, and benzonitrile; ethers such as diethyl ether, diisopropyl ether, methyl tert-butyl ether (MTBE), tetrahydrofuran, and dioxane; aromatic hydrocarbons such as benzene, toluene, and xylene; and carboxylic acids such as acetic acid and propionic acid. Alcohols, ethers, nitriles and carboxylic acids are preferred, with alcohols and ethers being more preferred, and methanol, ethanol, isopropanol, dioxane, dimethoxyethane, and tetrahydrofuran being still more preferred. These organic solvents may be used alone or in combination of two or more thereof.

The amount of the solvent used is, for example, in the range of 0.1 to 100 mL, preferably in the range of 1 to 50 mL, relative to 1 g of N-benzyl-4-pentafluorosulfanylbenzene or (4-pentafluorosulfanylphenyl)hydrazine.

Examples of the catalyst used at the reduction step include platinum group metals such as Pd, Pt, Rh, Ru, and Raney nickel, with Pd/C or Raney nickel on activated carbon being preferred.

The amount of the catalyst used is, for example, in the range of 0.01 to 100 g, preferably in the range of 0.1 to 5 g, relative to 1 g of N-benzyl-4-pentafluorosulfanylbenzene or (4-pentafluorosulfanylphenyl)hydrazine.

The reaction temperature is in the range of 0 to 200° C., preferably in the range of 10 to 180° C., more preferably in the range of 20 to 150° C.

Hydrogen is supplied through a resin balloon or a pipe, but may also be generated and used in the reaction system.

The reaction pressure is in the range of 1 to 10 atmospheres (atm), preferably in the range of 1 to 5 atm.

After completion of the reaction, the reaction product can be purified by a common technique such as neutralization, extraction, filtration, concentration, distillation, or column chromatography to obtain a pentafluorosulfanylaniline compound of interest.

By hydrolyzing the product (i.e., (4-pentafluorosulfanylphenyl)guanidine or N-(4-pentafluorosulfanylphenyl)phthalimide) obtained at the aforementioned nucleophilic reaction step, pentafluorosulfanylaniline is produced. This step may also be referred to as a "hydrolysis step".

The hydrolysis is carried out using an aqueous acid solution or an aqueous alkali solution. Examples of the aqueous acid solution include aqueous solutions of hydrogen chloride, hydrogen bromide, hydrogen iodide, sulfuric acid, nitric acid, methanesulfonic acid, trifluoromethanesulfonic acid, acetic acid, trifluoroacetic acid, or formic acid.

Examples of the aqueous alkali solution include aqueous solutions of a hydroxide, carbonate, bicarbonate, or the like of an alkali metal (e.g., sodium, potassium) or alkaline-earth metal (e.g., calcium). Examples of the hydroxide of an alkali metal include sodium hydroxide and potassium hydroxide. Examples of the carbonate of an alkali metal include sodium carbonate and potassium carbonate. Examples of the bicarbonate of an alkali metal include sodium bicarbonate and potassium carbonate.

Examples of the hydroxide of an alkaline-earth metal include calcium hydroxide. Examples of the carbonate of an alkaline-earth metal include calcium carbonate. Examples of the bicarbonate of an alkaline-earth metal include calcium bicarbonate.

The amount of the aqueous acid solution or aqueous alkali solution used is in the range of 0.0001 to 100 mL, preferably in the range of 0.001 to 50 mL, relative to 1 g of the reaction mixture obtained by the aforementioned nucleophilic reaction or the product obtained by purifying said mixture as mentioned above. When the reaction solution obtained at the nucleophilic reaction step is used as it is, an organic solvent may be present in the reaction solution.

The reaction temperature of the hydrolysis is in the range of 0 to 200° C., preferably in the range of 10 to 150° C.

After completion of the reaction, the reaction product can be purified by a common technique such as neutralization, extraction, filtration, concentration, distillation, or column chromatography to obtain a pentafluorosulfanylaniline compound of interest.

EXAMPLES

Example 1

A 500 mL glass vessel equipped with a stirrer and a condenser tube was charged with 20 g of 4-fluoro-pentafluorosulfanylbenzene, 100 mL of dimethyl sulfoxide, 30 mL of benzylamine, and 38 g of potassium carbonate, and the contents were reacted under stirring for 30 hours with heating to 130° C. (reaction solution A). Toluene was added, inorganic salts were filtered off, and the filtrate was washed with water. The resulting mother liquor was concentrated to dryness to obtain 32 g of a crude product. The NMR quantification of the crude product confirmed that 24 g (yield: 88%) of N-benzyl-4-pentafluorosulfanylbenzene was produced.

Thirty-two grams of the crude product was dissolved with 96 mL of methanol by heating to 50° C., and was crystallized by adding 27 mL of water slowly to obtain 26 g of a crude crystal. The crude crystal was dissolved in 125 mL of methanol, 6.3 g of activated carbon was added, and the mixture was refluxed by heating for 30 minutes. After cooling to room temperature, the solution was filtered over celite to filter out activated carbon, and the filtrate was concentrated to give white solids. The white solids were dissolved with 75 mL of methanol by heating to 60° C., and were crystallized by adding 20 mL of water slowly to yield 22 g of a white powder.

The property values of N-benzyl-4-pentafluorosulfanylbenzene are as shown below.

$^1$H-NMR (400 MHz; CDCl$_3$; δ (ppm)) 4.36 to 4.37 (m, 2H), 4.46 (brs, 1H), 6.54 to 6.56 (m, 2H), 7.25 to 7.39 (m, 5H), 7.51 to 7.53 (m, 2H)

EI-MS; 309 (M)

Example 2

The same procedure as in Example 1 was repeated except that dimethyl sulfoxide was replaced by N-methyl-2-pyrrolidone. The yield was 92%.

Example 3

The same procedure as in Example 1 was repeated except that potassium carbonate was replaced by diisopropylethylamine. The yield was 76%.

Example 4

The same procedure as in Example 1 was repeated except that benzylamine was replaced by para-methoxybenzylamine N-(4-methoxybenzyl)-4-pentafluorosulfanylbenzene was obtained in a yield of 86%.

The property values of N-(4-methoxybenzyl)-4-pentafluorosulfanylbenzene are as shown below.

$^1$H-NMR (400 MHz; CDCl$_3$; δ (ppm)) 3.81 (s, 3H), 4.28 to 4.29 (m, 2H), 4.38 (brs, 1H), 6.53 to 6.56 (m, 2H), 6.88 to 6.90 (m, 2H), 7.25 to 7.27 (m, 2H), 7.51 to 7.53 (m, 2H)

EI-MS; 339 (M)

Example 1a

Four grams (80 mmol) of hydrazine was added to the reaction solution A prepared in Example 1, and the mixture was stirred under heating at 50° C. for 5 hours. After cooling to room temperature, toluene was added, inorganic salts were filtered off, and the filtrate was washed with saturated saline (200 mL, five times) and 1N hydrochloric acid (200 ml, five times). The resulting mother liquor was concentrated to dryness to obtain 27 g of yellow solids. The NMR quantification of the solids confirmed that 26 g (yield: 92%) of N-benzyl-4-pentafluorosulfanylbenzene was produced.

Example 5 (Reduction Reaction of 4-benzyl Compound)

Ten milliliters of ethanol and 0.40 g of a dry 10% Pd/C catalyst were added to 1 g of N-benzyl-4-pentafluorosulfanylbenzene obtained in Example 1, and the mixture was stirred under heating at 50° C. for 4 hours in a hydrogen atmosphere. After Pd/C was filtered off, the filtrate was concentrated to dryness to obtain 0.65 g of 4-pentafluorosulfanylaniline as white solids in a yield of 92%.

The property values of 4-pentafluorosulfanylaniline are as shown below.

$^1$H-NMR (400 MHz; CDCl$_3$; δ (ppm)) 4.00 (brs, 2H), 6.61 to 6.63 (m, 2H), 7.51 to 7.53 (m, 2H)

EI-MS; 219 (M)

Example 6

Five milliliters of ethanol and 0.4 g of a dry 10% Pd/C catalyst were added to 1.0 g of N-benzyl-4-pentafluorosulfanylbenzene obtained in Example 1a, and the mixture was stirred at room temperature for 1 hour in a hydrogen atmosphere. The analysis by HPLC showed that 4-pentafluorosulfanylaniline was produced with a percent area of 100%.

Example 7

A 100 mL glass vessel equipped with a stirrer and a condenser tube was charged with 5 g of 2-fluoro-pentafluorosulfanylbenzene, 25 mL of dimethyl sulfoxide, 7.23 g of benzylamine, and 9.33 g of potassium carbonate, and the contents were reacted with stirring overnight under heating at 130° C. 0.5 g (10 mmol) of hydrazine was added to the reaction solution, and the mixture was stirred under heating at 50° C. for 2 hours. After cooling to room temperature, toluene was added, inorganic salts were filtered off, and the filtrate was washed with saturated saline (50 mL, five times) and 1N hydrochloric acid (50 mL, five times). The resulting mother liquor was concentrated to dryness to obtain 1.41 g of yellow solids. The NMR quantification of the solids confirmed that N-benzyl-2-pentafluorosulfanylbenzene was obtained in an isolation yield of 20%.

$^1$H-NMR (400 MHz; CDCl$_3$; δ (ppm)) 4.44 to 4.45 (m, 2H), 5.29 (brs, 1H), 6.66 to 6.75 (m, 2H), 7.23 to 7.39 (m, 6H), 7.62 to 7.64 (m, 1H)

EI-MS; 309 (M)

Example 8

A 100 mL glass vessel equipped with a stirrer and a condenser tube was charged with 5 g (22.5 mmol) of 4-fluoro-pentafluorosulfanylbenzene, 15 mL of dimethyl sulfoxide, and 3.3 mL (67.5 mmol) of hydrazine monohydrate, and the contents were reacted at 75° C. for 1 hour and at 95° C. for 2 hours. After cooling to room temperature, the reaction solution was added to 50 mL of a 1N aqueous solution of sodium hydroxide, and the mixture was cooled to 0° C. to precipitate solids, which were filtered off under reduced pressure, washed with water, and dried under vacuum at room temperature, whereby 4.5 g of (4-pentafluorosulfanylphenyl)hydrazine was obtained as white solids (isolation yield: 85%).

The property values of (4-pentafluorosulfanylphenyl)hydrazine are as shown below.

$^1$H-NMR (400 MHz; CDCl$_3$; δ (ppm)) 3.63 (brs, 2H), 5.50 (brs, 1H), 6.78 to 6.80 (m, 2H), 7.56 to 7.60 (m, 2H)

EI-MS; 234 (M)

Example 9

A 30 mL glass vessel equipped with a stirrer and a condenser tube was charged with 1 g (4.5 mmol) of 4-fluoro-pentafluorosulfanylbenzene, 1 mL of dimethyl sulfoxide, and 0.7 mL (13.5 mmol) of hydrazine monohydrate, and the contents were reacted at 95° C. for 6 hours. The quantification by HPLC showed that 0.86 g of (4-pentafluorosulfanylphenyl)hydrazine was produced (reaction yield: 81%).

Examples 10 to 16

Likewise, (4-pentafluorosulfanylphenyl)hydrazines were obtained by the same procedure as in Example 9 except that the conditions shown below were adopted.

TABLE 1

| | (eq.) Hydrazine | Solvent | (v/w) Amount | (eq.) K$_2$CO$_3$ | (° C.) Temp. | (hr) Time | (%) Yield |
|---|---|---|---|---|---|---|---|
| Example 9 | 3 | DMSO | 1 | 0 | 95 | 6 | 81 |
| Example 10 | 3 | DMSO | 0.5 | 0 | 95 | 6 | 66 |
| Example 11 | 3 | DMSO | 2 | 0 | 95 | 6 | 90 |

TABLE 1-continued

| | (eq.) Hydrazine | Solvent | (v/w) Amount | (eq.) K$_2$CO$_3$ | (° C.) Temp. | (hr) Time | (%) Yield |
|---|---|---|---|---|---|---|---|
| Example 12 | 1 | DMSO | 2 | 0 | 95 | 6 | 65 |
| Example 13 | 3 | DMSO | 3 | 0 | 95 | 6 | 80 |
| Example 14 | 3 | DMSO | 1 | 1 | 95 | 6 | 50 |
| Example 15 | 4 | DMSO | 1 | 0 | 115 | 6 | 78 |
| Example 16 | 3 | NMP | 2 | 0 | 95 | 6 | 86 |

Example 17

A 30 mL glass vessel equipped with a stirrer and a condenser tube was charged with 1 g (4.5 mmol) of 4-fluoro-pentafluorosulfanylbenzene, 15 mL of dimethyl sulfoxide, 1.22 g (6.8 mmol) of guanidine carbonate, and 1.86 g (13.5 mmol) of potassium carbonate, and the contents were reacted at 130° C. for 17 hours. As a result of analysis of the reaction solution, it was shown that (4-pentafluorosulfanylphenyl)guanidine and 4-pentafluorosulfanylaniline were produced with HPLC percent areas of 87% and 13%, respectively.

The property values of (4-pentafluorosulfanylphenyl)guanidine are as shown below.

$^1$H-NMR (400 MHz; CDCl$_3$; δ (ppm)) 6.96 to 6.98 (m, 2H), 7.59 to 7.61 (m, 2H)

EI-MS; 261 (M)

Further, as a result of analysis of the reaction solution after reaction at 130° C. for 48 hours, it was shown that (4-pentafluorosulfanylphenyl)guanidine and 4-pentafluorosulfanylaniline were produced with HPLC percent areas of 59% and 41%, respectively.

Example 18

A 30 mL glass vessel equipped with a stirrer and a condenser tube was charged with 1 g (4.5 mmol) 4-fluoro-pentafluorosulfanylbenzene, 5 mL of dimethyl sulfoxide, and 1.0 g (5.4 mmol) of potassium phthalimide, and the contents were reacted at 100° C. for 1 hour and at 130° C. for 18 hours. Thereafter, 2.0 g (10.8 mmol) of potassium phthalimide and 5 mL of dimethyl sulfoxide were added, and the mixture was reacted at 130° C. for 3 hours. After cooling to room temperature, the reaction solution was added to 50 mL of a 1N aqueous solution of sodium hydroxide, and the precipitated sediment was filtered off and dried to yield 0.1 g N-(4-pentafluorosulfanylphenyl)phthalimide as white solids (isolation yield: 6%).

The property values of N-(4-pentafluorosulfanylphenyl)phthalimide are as shown below.

$^1$H-NMR (400 MHz; CDCl$_3$; δ (ppm)) 7.64 to 7.66 (m, 2H), 7.82 to 7.86 (m, 2H), 7.89 to 7.93 (m, 2H), 7.97 to 8.01 (m, 2H)

EI-MS; 349 (M)

Example 19

A 30 mL glass vessel equipped with a stirrer and a condenser tube was charged with 0.25 g (1.1 mmol) of (4-pentafluorosulfanylphenyl)hydrazine, 0.05 g of Raney nickel, and 5 mL of ethanol, and the contents were reacted at room temperature for 1 hour and then at 70° C. for 2 hours while hydrogen was supplied through a hydrogen balloon. After Raney nickel was filtered off, the solution was concentrated to dryness to obtain 0.19 g of 4-pentafluorosulfanylaniline as white solids (isolation yield: 83%).

Example 20

A 100 mL glass vessel equipped with a stirrer and a condenser tube was charged with 15 g (67.5 mmol) of 4-fluoro-pentafluorosulfanylbenzene, 30 mL of dimethyl sulfoxide, 9.8 mL (203 mmol) of hydrazine monohydrate, and the contents were reacted at 95° C. for 5.5 hours. After cooling to room temperature, 100 mL of a 1N aqueous solution of sodium hydroxide and 100 mL of saturated saline were added, and the mixture was extracted with 150 mL of MTBE (methyl tert-butyl ether), and then the extract was washed with 100 mL of saturated saline three times. After drying over magnesium sulfate, the solution was concentrated under reduced pressure at 40° C. to obtain 14.97 g of (4-pentafluorosulfanylphenyl)hydrazine as yellow solids (isolation yield: 95%). To 14.97 g of the yellow solids obtained, 3 g of Raney nickel and 300 mL of isopropanol were added, and the mixture was reacted at 60° C. for 1 hour and at 70° C. for 3 hours while hydrogen was supplied through a resin balloon. Then, 0.7 g of Raney nickel was added, and the mixture was reacted at 60° C. for 1 hour. After completion of the reaction, Raney nickel was filtered off, and the remaining solution was concentrated under reduced pressure to obtain 13.1 g of 4-pentafluorosulfanylaniline (isolation yield based on 4-fluoro-pentafluorosulfanylbenzene: 94%).

Example 21

A 100 mL glass vessel equipped with a stirrer and a condenser tube was charged with 15 g (67.5 mmol) of 2-fluoro-pentafluorosulfanylbenzene, 30 mL of dimethyl sulfoxide, and 9.8 mL (203 mmol) of hydrazine monohydrate, and the contents were reacted at 100° C. for 3 hours. Then, 9.8 mL (203 mmol) of hydrazine monohydrate and 15 mL of dimethyl sulfoxide were added, and the mixture was further reacted for 10 hours. After cooling to room temperature, 100 mL of a 1N aqueous solution of sodium hydroxide and 100 mL of saturated saline were added, and the mixture was extracted with 150 mL of MTBE (methyl tert-butyl ether), and then the extract was washed with 100 mL of saturated saline three times. After drying over magnesium sulfate, the solution was concentrated under reduced pressure at 40° C. to obtain 13.9 g of (2-pentafluorosulfanylphenyl)hydrazine as yellow solids (isolation yield: 88%).

(2-Pentafluorosulfanylphenyl)hydrazine is a novel compound having the property values shown below.

$^1$H-NMR (400 MHz; $CDCl_3$; δ (ppm)) 3.63 (brs, 2H), 6.25 (brs, 1H), 6.74 to 6.78 (m, 1H), 7.37 to 7.41 (m, 1H), 7.46 to 7.48 (m, 1H), 7.59 to 7.61 (m, 1H)

EI-MS; 234 (M)

1 g of the above-obtained product (2-pentafluorosulfanylphenyl)hydrazine was reacted with a total of 1.5 g of Raney nickel at 70 to 80° C. for 6 hours using 10 mL of isopropanol while hydrogen was supplied through a resin balloon, wherein the Raney nickel was added sequentially. As a result, it was observed that 2-pentafluorosulfanylaniline was produced.

The property value of 2-pentafluorosulfanylaniline is as shown below.

EI-MS; 219 (M)

Example 22

A glass reaction vessel with a volume of 30 mL was charged with 1.51 g (6.8 mmol) of 3-fluoropentafluorosulfanylbenzene, 1.01 g (20.8 mmol) of hydrazine monohydrate, and 3 mL of dimethyl sulfoxide, and the contents were reacted at 80° C. for 4 hours and then at 110° C. for 3 hours. Next, 1.01 g (20.8 mmol) of hydrazine monohydrate was added, and the mixture was further reacted at 110° C. for 8 hours. After the reaction solution was cooled to room temperature, 100 mL of a 1N aqueous solution of sodium hydroxide was added, and the liquid mixture was separated by adding 100 mL of tert-butyl methyl ether and 100 mL of saturated saline, and then the organic layer was washed with 100 mL of saturated saline three times. After the organic layer was dried with anhydrous magnesium sulfate, the solvent was distilled off under reduced pressure to obtain 1.04 g of 3-hydrazinopentafluorosulfanylbenzene as a light yellow oil (isolation yield: 65%).

3-Hydrazinopentafluorosulfanylbenzene is a novel compound having the property values shown below.

$^1$H-NMR ($CDCl_3$): 3.64 (brs, 2H), 5.38 (brs, 1H), 6.91 to 6.94 (m, 1H), 7.15 to 7.17 (m, 1H), 7.25 to 7.29 (m, 2H)

EI-MS; 234 (M+1)

Example 23

A glass reaction vessel with a volume of 30 mL was charged with 0.52 g (2.22 mmol) of 3-hydrazinopentafluorosulfanylbenzene, 0.2 g of Raney nickel (produced by Tokyo Chemical Industry Co., Ltd.), and 20 mL of ethanol, and the contents were reacted at room temperature for 4 hours under pressure applied by a hydrogen balloon. After completion of the reaction, inorganic matter was filtered off over celite, the solvent was distilled off, and traces of insoluble matter were removed using a membrane filter, whereby 0.3 g of 3-aminopentafluorosulfanylbenzene was obtained as a light yellow oil (isolation yield: 67%).

3-Aminopentafluorosulfanylbenzene is a compound having the property values shown below.

$^1$H-NMR ($CDCl_3$): 3.81 (brs, 2H), 6.72 to 6.75 (m, 1H), 7.01 to 7.02 (m, 1H), 7.08 to 7.11 (m, 1H), 7.16 to 7.20 (m, 1H)

EI-MS; 219 (M+1)

The reaction scheme of Examples 22 and 23 is shown below.

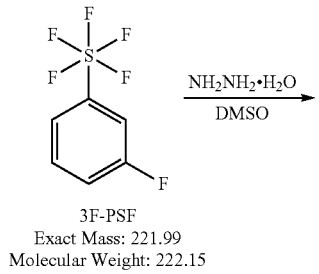

3F-PSF
Exact Mass: 221.99
Molecular Weight: 222.15

-continued

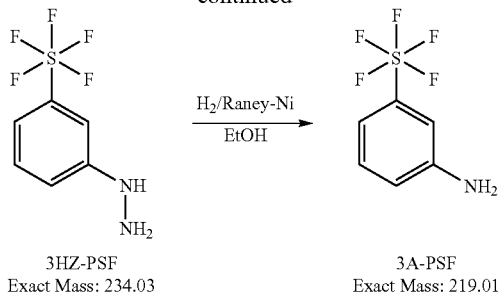

3HZ-PSF
Exact Mass: 234.03
Molecular Weight: 234.19

3A-PSF
Exact Mass: 219.01
Molecular Weight: 219.17

The invention claimed is:

1. A method for producing a nitrogen-containing pentafluorosulfanylbenzene compound of formula (2a) or (2b):

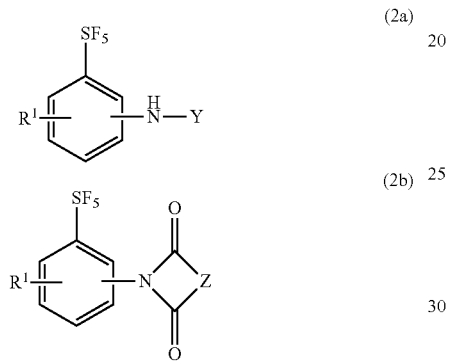

(wherein $R^1$ a hydrogen atom or a hydrocarbon group; Z is an aryl group linked to a carbonyl group; Y is a group of formula (Y1), (Y2), (Y3), or (Y4); $R_2$ is a hydrogen atom or a hydrocarbon group)

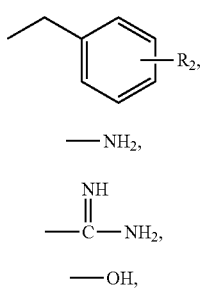

the method comprising reacting a halogeno-pentafluorosulfanylbenzene compound of formula (1) with a nitrogenous nucleophile:

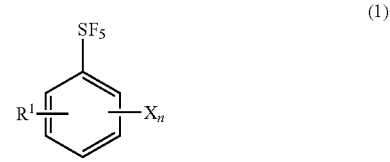

(wherein X is a halogen atom; n is an integer of 1 to 5; $R^1$ is as defined above).

2. A method for producing a pentafluorosulfanylaniline compound of formula (3):

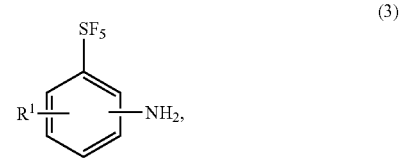

the method comprising reducing or hydrolyzing the nitrogen-containing pentafluorosulfanylbenzene compound as set forth in claim 1.

3. The method according to claim 1, wherein the nitrogenous nucleophile is at least one member selected from benzylamine compounds, hydrazine compounds, guanidine compounds, hydroxylamines and alkali metal salts of phthalimide.

4. The method according to claim 2, wherein the reduction is carried out in the presence of hydrogen using Pd/C or Raney nickel as a catalyst.

5. The method according to claim 2, wherein the hydrolysis is carried out using an aqueous acid solution or an aqueous alkali solution.

6. The method according to claim 1, wherein an aprotic polar solvent is used as a solvent.

7. The method according to claim 6, wherein the aprotic polar solvent is dimethyl sulfoxide or N-methyl-2-pyrrolidone.

8. The method according to claim 1, wherein a base is used in the reaction of the halogeno-pentafluorosulfanylbenzene compound with the nitrogenous nucleophile.

* * * * *